US00PP19332P3

(12) United States Plant Patent
Danziger

(10) Patent No.: US PP19,332 P3
(45) Date of Patent: Oct. 14, 2008

(54) ***LOBELIA* PLANT NAMED 'DANANAB2'**

(50) Latin Name: *Lobelia erinus*
Varietal Denomination: DANANAB2

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/717,734

(22) Filed: Mar. 14, 2007

(65) Prior Publication Data

US 2008/0229462 P1 Sep. 18, 2008

(51) Int. Cl.
*A01H 5/00* (2006.01)

(52) U.S. Cl. ..... Plt./451; Plt./263

(58) Field of Classification Search ..... Plt./451, Plt./263

See application file for complete search history.

*Primary Examiner*—Annette H Para
*Assistant Examiner*—S. B. McCormick-Ewoldt
(74) *Attorney, Agent, or Firm*—Foley & Lardner LLP

(57) ABSTRACT

A new and distinct *Lobelia* plant named 'DANANAB2', particularly characterized by trailing growth habit; blue flowers with a white center; green leaves, glossy in texture; and heat tolerant.

2 Drawing Sheets

Latin name of the genus and species of the claimed plant: *Lobelia erinus.*
Variety denomination: 'DANANAB2'.

BACKGROUND OF THE INVENTION

The present invention relates to a new and distinct cultivar of *Lobelia* plant, botanically known as *Lobelia erinus,* hereinafter referred to by the cultivar name 'DANANAB2'.

*Lobelia,* of the Campanulaceae family, consists of over 200 species, of both annuals and perennials, which can be grown in both the Northern and Southern hemispheres.

The new *Lobelia* cultivar is a product of a planned breeding program conducted by the inventor, Gabriel Danziger, in Moshav Mishmar Hashiva, Israel. The objective of the breeding program is to develop a new perennial *Lobelia* variety with a trailing growth habit.

The new *Lobelia* cultivar originated from open pollination in a controlled breeding program by the inventor in 2004, in Moshav Mishmar Hashiva, Israel. Open pollination of the unpatented seed parent, *Lobelia* cultivar 'CV-241', by an unknown *Lobelia* cultivar, was conducted in a controlled breeding program in Moshav Mishmar Hashiva, Israel. The new *Lobelia* cultivar 'DANANAB2' was discovered and selected by the inventor, Gabriel Danziger, as a single flowering plant within the progeny of the stated cross in a controlled environment in Moshav Mishmar Hashiva, Israel.

Asexual reproduction of the new *Lobelia* cultivar by vegetative cutting was first performed in May of 2005 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DANANAB2', which in combination distinguish this *Lobelia* as a new and distinct cultivar:

1. Trailing growth habit;
2. Blue flowers with a white center;
3. Green leaves, glossy in texture; and
4. Heat Tolerant.

Plants of the new *Lobelia* 'DANANAB2' differ from plants of the parental cultivar 'CV-241' (unpatented) in the characteristics described in Table 1.

TABLE 1

| Characteristic | New Cultivar 'DANANAB2' | Female Parent Cultivar 'CV-241' (Unpatented) |
|---|---|---|
| Flower Color | Blue With White Center (Darker blue than female parent cultivar) | Blue |
| Plant Habit | Trailing | Erect |
| Leaves | Glossy Green Color | Matte Green Color |

Of the many commercial cultivars known to the present inventor, the most similar in comparison to the new *Lobelia* 'DANANAB2' is the *Lobelia* cultivar 'HOT WHITE SPOT' (unpatented) in the characteristics described in Table 2.

TABLE 2

| Characteristic | New Cultivar 'DANANAB2' | Comparison Cultivar 'HOT WHITE SPOT' (unpatented) |
|---|---|---|
| Flower Color | Blue With White Center (Darker blue than comparison cultivar) | Blue With White Center |

TABLE 2-continued

| Characteristic | New Cultivar 'DANANAB2' | Comparison Cultivar 'HOT WHITE SPOT' (unpatented) |
|---|---|---|
| Plant Habit | Trailing | Erect |
| Leaves | Glossy Green Color | Matte Green Color |
| Branches | Thin and flexible | Thick and less flexible |

BRIEF DESCRIPTION OF THE PHOTOGRAPHS

The accompanying photographs illustrate the overall appearance of the new *Lobelia* 'DANANAB2' showing the colors as true as is reasonably possible with colored reproductions of this type. Colors in the photographs may differ slightly from the color value cited in the detailed botanical description, which accurately describe the color of 'DANANAB2'.

DETAILED BOTANICAL DESCRIPTION

Figure 1:
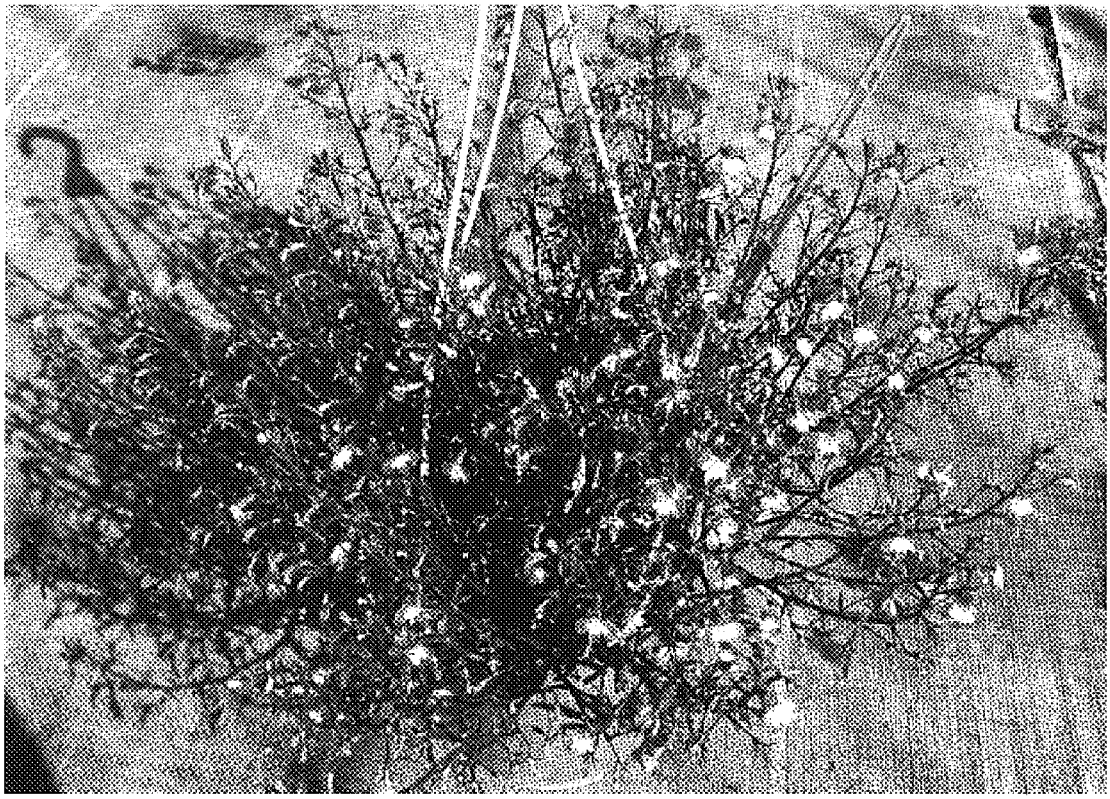
FIG. 1 shows a top view perspective of a typical flowering plant of 'DANANAB2' in a hanging planter at 3 months of age.
Figure 2:
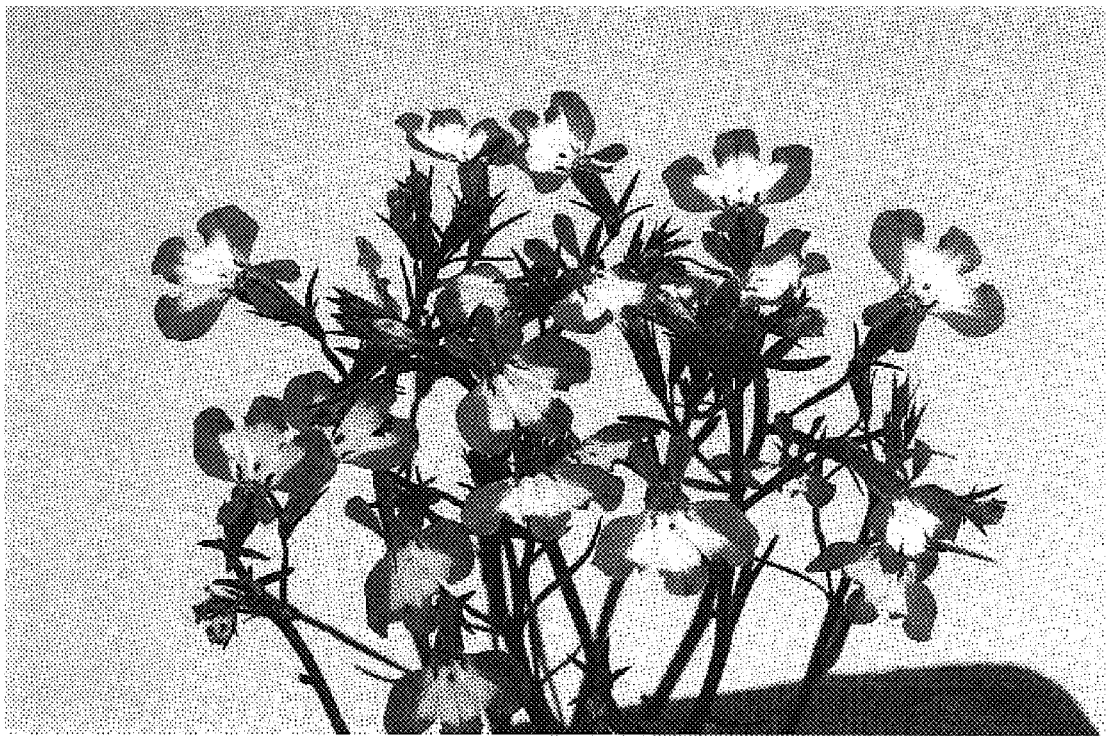
FIG. 2 shows a close-up view of the typical flowers and buds of 'DANANAB2' at 3 months of age.

The new *Lobelia* 'DANANAB2' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Lobelia* 'DANANAB2' as grown in a greenhouse in Moshav Mishmar Hashiva, Israel, under conditions which closely approximate those generally used in commercial practice. Plants of the new *Lobelia* 'DANANAB2' are grown in conditions of day length of 11 to 18 hours, and with day temperatures ranging from 18° C. to 25° C. and night temperatures ranging from 12° C. to 18° C. A balanced fertilizer of 75 to 200 ppm N, according to the growing stage, is used.

Color references are made to The Royal Horticultural Society Colour Chart (R.H.S.), 2001 edition, except where general terms of ordinary significance are used. Color values were taken under daylight conditions at approximately 12:00 noon in Moshav Mishmar Hashiva, Israel. The age of the plant described is 4 months.

Classification:
- *Botanical.*—*Lobelia erinus.*

Parentage:
- *Female or seed parent.*—*Lobelia* 'CV-241' (unpatented).
- *Male or pollen parent.*—Open pollination; unknown *Lobelia* cultivar.

Optimal growth conditions:
- *Light intensities.*—Full sunlight or slight shade.
- *Temperature.*—Day: 18° C. to 25° C. Night: 12° C. to 18° C.
- *Temperature tolerance.*—Tolerant to a low temperature of about 5° C. and tolerant to a high temperature of about 35° C.
- *Fertilization.*—A balanced fertilizer application beginning an application of 75 to 100 ppm N when roots become visible, followed by an increased application of 150 to 200 ppm N as roots develop. Avoid phosphorous and ammoniacal nitrogen during the rooting process to reduce unwanted vegetative growth.
- *Growth regulator.*—ALAR 2 g/L.

Propagation:
- *Type.*—Cuttings of side shoots.
- *Rooting description.*—Fibrous, freely branching, white in color, RHS 155D.
- *Time to initiate roots.*—About 6 to 10 days at 18° C.
- *Time to produce a rooted cutting.*—About 16 days at 18° C.

Plant: General Appearance and Form is mounded to trailing growth habit.
- *Height* (*from top of soil, including flowers*).—About 20 cm.
- *Spread.*—About 60 cm.
- *Vigor.*—Medium.
- *Crop time.*—After rooting, about 3 to 8 weeks are required to produce a finished flowering pot.
- *Fragrance.*—None.
- *Stem.*—Length: About 20 cm. Diameter: About 4 mm. Texture: glabrous. Color: Green, RHS 139A. Stem anthocyanin: Absent.
- *Pedicel.*—Length: About 5 cm. Diameter: About 1 mm. Texture: Glabrous. Color: Green, RHS 139A.
- *Branching habit.*—Medium. Lateral branches: Quantity per plant: About 50. Length: About 20 cm. Diameter: About 4 mm. Texture: Glabrous. Color: Green, RHS 139A. Length of Internodes: 1.5 to 4 cm.

Foliage:
- *Arrangement.*—Alternate.
- *Leaf length.*—About 5 cm.
- *Leaf width.*—About 1.0 to 1.5 cm.
- *Overall shape of leaf.*—Lanceolate.
- *Apex shape.*—Obtuse.
- *Base shape.*—Cuneate.
- *Margin.*—Serrate.
- *Texture.*—Upper Surface: Glabrous. Lower Surface: Glabrous.
- *Pubescence* (*both surfaces*).—None.
- *Color of mature leaf.*—Upper Surface: Green, RHS 137A. Lower Surface: Green, RHS 137C.
- *Color of immature leaf.*—Upper Surface: Green, RHS 137A. Lower Surface: Green, RHS 137C.
- *Venation.*—Pattern: Palmate. Color: Upper surface: Green, RHS 137A. Lower surface: Green, RHS 137B.

Inflorescence description:
- *Natural flowering season.*—Flowering occurs continuously during growing season from spring until fall. Flowering occurs between February to November outdoors in Israel.
- *Lastingness of individual blooms on plant.*—Depending on weather conditions, 7 to 14 days for single flower and about 250 days for the whole plant (all season).
- *Fragrance.*—None.
- *Quantity of flowers and buds per lateral branch.*—About 6 open flowers and 4 buds.
- *Flower bud* (*about* 4 *days prior to opening*).—Shape: Spatulate. Length: About 12 mm. Diameter: About 2 mm. Texture: Smooth. Color: Yellow-green, RHS 149B.
- *Inflorescence description.*—Flowers form at apical axils, with one flower per axil. Flowers are labiates; upper petal has two small lobes and lower lip has three larger and broader lobes, which are fused at base.

*Corolla size.*—Diameter (spread): About 2 cm. Diameter at lobes: About 8 mm. Overall flower height: About 5 mm. Length of corolla tube: About 10 mm. Diameter of corolla tube: About 5 mm.

*Upper lobes (the 2 small lobs).— Length: About* 7 mm. Width: About 1 mm. Overall shape: elliptic. Apex: Obtuse. Base: Cuneate. Margin: Entire. Texture (upper & lower surfaces): glabrous. Color: Upper surface, when opening: Blue, RHS 105A. Upper surface, opened flower: Blue, RHS 105A. Lower surface, when opening: Blue, RHS 105C. Lower surface, opened flower: Blue, RHS 105C.

*Lower lobes.*—Length: About 12 mm. Width: About 5 mm. Overall shape: Oval. Apex: Blunt. Base: Cuneate. Margin: Entire. Texture (upper & lower surfaces): Glabrous.

*Color.*—Center: Upper surface, when opening: Blue, RHS 102B, with white center, with blue dot, RHS 102B, in the center of white center toward apex. Upper surface, opened flower: Blue, RHS 102B, with white center, with blue dot, RHS 102B, in the center of white center toward apex. Lower surface, when opening: Blue, between RHS 102B to RHS 102C, with white, RHS 155D. Lower surface, opened flower: Blue, between RHS 102B to RHS 102C, with white, RHS 155D. Two Sides: Upper surface, when opening: Blue, RHS 102B, with white at lobe side parallel to white of center lobe, with blue crescent dot, RHS 102B, near apex of white section. Upper surface, opened flower: Blue, RHS 102B, with white at lobe side parallel to white of center lobe, with blue crescent dot, RHS 102B, near apex of white section. Lower surface, when opening: Blue, between RHS 102B to RHS 102C, with white, RHS 155D. Lower surface, opened flower: Blue, between RHS 102B to RHS 102C, with white, RHS 155D.

*Flower throat color.*—Blue, ranging from RHS 100A to RHS100D.

*Flower throat texture.*—Glabrous.

*Corolla tube color.*—Blue, ranging from RHS 100A to RHS100D.

*Sepals.*—Length: About 10 mm. Width: About 1 mm. Overall shape: Ensiform. Apex: Acute. Base: Cuneate. Margin: Entire. Texture: Upper surface: Glabrous. Lower surface: Glabrous. Upper surface color: Green, RHS 139A. Lower surface color: Green, RHS 139A.

Reproductive organs:

*Androecium.*—Stamen: Number: 5. Color: Blue, ranging from RHS 100A to RHS 100D. Anthers: Shape Ellipsoid. Length: About 2 mm. Color: Violet-blue, RHS 95B. Filaments: Length: About 8 mm. Color: Blue, ranging from RHS 100A to RHS 100D. Pollen: Amount: Moderate. Color: Greyed-yellow, RHS 160A.

*Gynoecium.*—Pistils: Quantity: 1. Length: About 6 mm. Stigma: Shape: Tubular. Width: About 1 mm. Color: Green, RHS 141D. Style: Length: About 7 mm. Ovary: Shape: Tubular. Length: About 5 mm. Width: About 2 mm. Color: Green, RHS 137A.

Seeds:

*Quantity per fruit.*—About 30.
*Shape.*—Elliptic.
*Length.*—About 0.5 mm.
*Width.*—About 0.1 mm.
*Texture.*—Glabrous.
*Color.*—Brown, RHS 200C.

Fruit:

*Type.*—Capsule.
*Length.*—About 6 mm.
*Width.*—About 3 mm.
*Texture.*—Rough.
*Color.*—Greyed-orange, RHS 170B.

Disease/pest resistance: No information is currently available.

Disease/pest susceptibility: No information is currently available.

Low temperature tolerance: Tolerant to low temperature of about 2° C.

High temperature tolerance: Tolerant to high temperature of 35° C.

I claim:

1. A new and distinct *Lobelia* plant named 'DANANAB2', as illustrated and described herein.

* * * * *